United States Patent
Piquemal (10) Patent No.: US 10,465,250 B2
(45) Date of Patent: Nov. 5, 2019

(54) METHOD FOR DETERMINING THE SURVIVAL PROGNOSIS OF A PATIENT SUFFERING FROM PANCREATIC CANCER

(71) Applicant: ACOBIOM, Grabels (FR)

(72) Inventor: David Piquemal, Saint Christol les Ales (FR)

(73) Assignee: ACOBIOM, Grabels (FR)

( * ) Notice: Subject to any disclaimer, the term of this patent is extended or adjusted under 35 U.S.C. 154(b) by 31 days.

(21) Appl. No.: 15/505,790

(22) PCT Filed: Aug. 13, 2015

(86) PCT No.: PCT/FR2015/052207
§ 371 (c)(1),
(2) Date: Feb. 22, 2017

(87) PCT Pub. No.: WO2016/027029
PCT Pub. Date: Feb. 25, 2016

(65) Prior Publication Data
US 2018/0105881 A1    Apr. 19, 2018

(30) Foreign Application Priority Data
Aug. 22, 2014 (FR) ..................... 14 57934

(51) Int. Cl.
*C12Q 1/68* (2018.01)
*C12Q 1/6886* (2018.01)
*G01N 33/574* (2006.01)
*G01N 33/68* (2006.01)

(52) U.S. Cl.
CPC ..... *C12Q 1/6886* (2013.01); *G01N 33/57438* (2013.01); *G01N 33/6872* (2013.01); *C12Q 2600/106* (2013.01); *C12Q 2600/118* (2013.01); *C12Q 2600/158* (2013.01); *G01N 2333/914* (2013.01); *G01N 2333/91235* (2013.01); *G01N 2800/52* (2013.01)

(58) Field of Classification Search
None
See application file for complete search history.

(56) References Cited

U.S. PATENT DOCUMENTS

2008/0227663 A1* 9/2008 Tisone ................. B01J 19/0046
506/39
2014/0148350 A1* 5/2014 Spetzler ............... G01N 33/574
506/9

FOREIGN PATENT DOCUMENTS

EP         2716767 A1 *  4/2014
WO   WO-2015049377 A1 *  4/2015

OTHER PUBLICATIONS

The Free Dictionary definition for "measuring", available via Url: < thefreedictionary.com/measuring>, printed on Sep. 20, 2017.*
Johnson et al Circulation. 2013. 127: 799-810.*
Tsiaousidou et al., B7H4, HSP27 and DJ-1 molecular markers as prognostic factors in pancreatic cancer, Pancreatology, 13:564-569 (2013).
Fujita et al., Gene expression levels as predictive markers of outcome in pancreatic cancer after gemcitabine-based adjuvant chemotherapy, Neoplasia, 12(10):807-817 (2010).
Kracmarova et al., High expression of ERCC1, FLT1, NME4 and PCNA associated with poor prognosis and advanced stages in myelodysplastic syndrome, Leukemia & Lymphoma, 49(7):1297-1305 (2008).
Affymetrix, Data Sheet on GeneChip homan genome U133 arrays, pp. 1-8 (2003).
Takadate et al., Nm23/nucleoside diphosphate kinase-A as a potent prognostic marker in invasive pancreatic ductal carcinoma identified by proteomic analysis of laser micro-dissected formalin-fixed paraffin-embedded tissue, Clinical Proteomics, 9(8): pp. 1-12 (2012).
Schafer et al., Heat shock protei 27 as a prognostic and predictive biomarker in pancreatic ductal adenocarcinoma, J. Cell. Mol. Med., 16(8):1776-1791 (2012).
Oettle, Progress in the knowledge and treatment of advanced pancreatic cancer:From benchside to bedside, Cancer Treatment Reviews, 40:1039-1047 (2014).
Nordh et al., hENT1 expression is predictive of gemcitabine outcome in pancreatic cancer: A systematic review, World Journal of Gastroenterology, 20(26):8482-8490 (2014).
Bauer et al., Carbohydrate antigen 19-9 is a prognostic and predictive biomarker in patients with advanced pancreatic cancer who receive gemcitabine-containing chemotherapy, Cancer, 119(2):285-292 (2013).

* cited by examiner

Primary Examiner — Carla J Myers
(74) Attorney, Agent, or Firm — Browdy and Neimark, PLLC (57) ABSTRACT

The present invention relates to pancreatic cancer, and more particularly to the survival prognosis of a patient suffering from pancreatic cancer. The invention also aims to determine the suitability of said patient to receive a treatment for pancreatic cancer, in particular a treatment with gemcitabine. The invention also concerns a method for monitoring the effectiveness of a treatment for pancreatic cancer, and advantageously a treatment with gemcitabine, by implementing the method.

12 Claims, 3 Drawing Sheets

Specification includes a Sequence Listing.

METHOD FOR DETERMINING THE SURVIVAL PROGNOSIS OF A PATIENT SUFFERING FROM PANCREATIC CANCER

The Sequence Listing in ASCII text file format of 3,908 bytes in size, created on Sep. 14, 2018, with the file name "2018-09-18SequenceListing_PIQUEMAL1," filed in the U.S. Patent and Trademark Office on Sep. 18, 2018, is hereby incorporated herein by reference.

The present invention relates to pancreatic cancer, and more particularly to the survival prognosis of a patient suffering from pancreatic cancer.

The invention also aims to determine the suitability of said patient for receiving a treatment for pancreatic cancer, particularly treatment with gemcitabine.

With 43,920 new cases annually in the United States, and 37,390 deaths, mortality associated with pancreatic cancer is greater than 85%, which puts pancreatic cancer in fourth place in terms of cancer deaths in the United States in both men and women.

The incidence of pancreatic cancer has shown a marked increase in recent decades. Each year, about 60,000 persons in Europe, and more than 230,000 worldwide, are diagnosed with this disease.

Patients suffering from pancreatic cancer often have a poorer prognosis compared to other malignant tumours and types of cancer, partly because early detection is difficult.

At the time of diagnosis, most patients suffering from pancreatic ductal adenocarcinoma have a locally advanced or metastatic disease, and only 10 to 20% of cases are candidates for curative surgery.

The median survival following diagnosis is about 3 to 6 months; 5-year survival is considerably less than 5% and complete remission is extremely rare.

The current therapies approved or used in clinical practice in patients with pancreatic cancer are treatments based on gemcitabine, FOLFIRINOX or erlotinib.

Gemcitabine is a nucleoside analogue, administered intravenously at a dose of about 1000 mg/m$^2$. Treatment with gemcitabine usually forms part of the first-line treatments recommended for respectable pancreatic cancer (stage I-II), non-respectable locally advanced pancreatic cancer (stage III) and advanced metastatic pancreatic cancer (stage IV).

With gemcitabine, the median overall survival varies between 4.9 months and 8.3 months.

The limited success of the treatments, and the mortality rate, which is still high for some patients, emphasize the need for means for improving therapeutic targeting of the patients who might respond well to gemcitabine and who would tolerate gemcitabine well in this indication.

Treatment of pancreatic cancer with different compounds may have different degrees of efficacy, depending on the patient. However, to date, there is no means for predicting the clinical benefit of the different treatments available for a given patient.

Thus, there is still a need for tests that make it possible to select the right treatment for each patient, so as to give them the best chance of survival.

It might be desirable for said test to be a test that can be carried out regularly. If said test is non-invasive, that would be an additional advantage.

Work conducted by the inventors made it possible to identify a set of genes for which investigation of their level of expression makes it possible to evaluate the survival time of a patient suffering from pancreatic cancer.

Advantageously, this prediction also makes it possible to predict the chances of success of treatment with gemcitabine and to select patients likely to have a favourable response to treatment with gemcitabine.

Thus, investigation of the level of expression of said genes makes it possible to provide information regarding the suitability of administering treatment with gemcitabine to a patient suffering from pancreatic cancer.

One of the advantages of the invention is that the level of expression of said genes can be evaluated directly from a blood sample, advantageously of whole blood from the patient, taken previously.

This is particularly advantageous in the case of pancreatic cancer as it is very difficult to gain access to the tumour cells.

Moreover, the taking of blood samples (collection, stabilization and transport) can be standardized.

Finally, the use of whole blood is more reliable than the use of a blood fraction, for example peripheral blood mononuclear cells (PBMC), as it makes it possible to avoid the handling errors associated with preparation of said fractions. By "whole blood" is meant blood with all its constituents (plasma, red blood cells, white blood cells, platelets, etc.), as opposed to "blood fraction", which corresponds to a product obtained by separation of the individual components of the blood. The peripheral blood mononuclear cells are an example of a blood fraction.

The invention therefore relates to an in-vitro method for establishing a survival prognosis for a patient suffering from pancreatic cancer, comprising the following steps:
 a) measuring the level of expression of at least one marker gene selected from the group constituted by the NME4, ITPR3, SESN3, ARL4C and RPLP1 genes or homologous genes, in a blood sample taken previously from said patient;
 b) comparing the measured level of expression for the marker gene(s) selected in step a) in said patient against a reference threshold;
 c) evaluating the survival time for said patient.

The term "homologous" is defined in the present text as a polynucleotide sequence having a degree of identity of at least 80%, preferably 85%, more preferably 90%, and even more preferably 99% with the sequence of the wild-type (full-length) gene. The degree of identity refers to sequence identity between two sequences. Identity can be determined by comparing a position in each sequence that can be aligned for purposes of comparison. When an equivalent position in the sequences being compared is occupied by the same base, the molecules are identical at this position. Various algorithms and/or alignment programs can be used for determining the homology of two sequences, including FASTA and BLAST.

The method according to the invention allows a survival prognosis to be established for a patient suffering from pancreatic cancer.

According to the invention, steps a) to c) of the aforementioned method may be used for a patient suffering from pancreatic cancer who has received treatment, and particularly treatment based on gemcitabine, in order to predict or evaluate the efficacy and/or benefit of a treatment for pancreatic cancer in a patient suffering from said pathology, in particular in terms of life expectancy.

Thus, the invention also relates to an in-vitro method for predicting or evaluating the efficacy and/or benefit of treatment for pancreatic cancer in a patient suffering from said pathology, comprising the following steps:
 a) measuring the level of expression of at least one marker gene selected from the group constituted by the NME4, ITPR3, SESN3, ARL4C and RPLP1 genes or homologous genes, in a blood sample taken previously from said patient;

b) comparing the level of expression measured for the marker gene(s) selected in step a) in said patient against a reference threshold;

c) evaluating the survival time for said patient.

The method according to the invention is particularly suitable for predicting or evaluating the efficacy and/or benefit of treatment for pancreatic cancer with gemcitabine.

In the methods according to the invention, the reference threshold used in step c) for making the comparison is determined beforehand for each gene or each combination of genes.

The principle of the invention is based on the fact that the applicant was able to establish that investigation of the level of expression of at least one of the 5 genes (NME4, ITPR3, SESN3, ARL4C and RPLP1), advantageously of a combination of 2 to 5 of these genes, even more advantageously of a combination of all 5 genes, makes it possible to establish a survival prognosis for the patient. More particularly, the applicant established that by comparing data on the level of expression of at least one of the 5 genes (NME4, ITPR3, SESN3, ARL4C and RPLP1) or combination thereof, obtained from a blood sample from said patient being tested, with data that they themselves have established for the 5 genes considered or combination thereof on a reference population of patients suffering from pancreatic cancer, before or during the treatment, made it possible to establish a survival prognosis for the patient and monitor the patient's treatment.

The method according to the invention may be carried out on a blood sample from a patient, preferably on a sample of peripheral blood from said patient, said blood sample being taken prior to application of the method according to the invention. The peripheral blood is the blood that circulates through the heart, the arteries, the capillaries and the veins.

According to the invention, step a) of the method may be carried out by measuring the level of expression of 1 of the 5 genes (or homologous genes) from the group defined above, advantageously 2 of the 5 genes, more advantageously 3 of the 5 genes, even more advantageously 4 of the 5 genes, and preferably all 5 genes (or homologous genes) from the group defined above.

Thus, according to the invention, step a) of the method may be carried out by measuring the level of expression of at least one gene (or homologous gene) selected from the NME4, ITPR3, SESN3, ARL4C and RPLP1 genes, advantageously of at least one of the following combinations: NME4 and ITPR3; NME4 and SESN3; NME4 and ARL4C; NME4 and RPLP1; ITPR3 and SESN3; ITPR3 and ARL4C; ITPR3 and RPLP1; SESN3 and ARL4C; SESN3 and RPLP1; ARL4C and RPLP1: more advantageously the level of expression of the genes of one of the following combinations: NME4 and ITPR3 and SESN3: NME4 and ITPR3 and ARL4C; NME4 and ITPR3 and RPLP1; NME4 and SESN3 and ARL4C: NME4 and SESN3 and RPLP1; NME4 and ARL4C and RPLP1; ITPR3 and ARL4C and RPLP1; ITPR3 and SESN3 and RPLP1; ITPR3 and SESN3 and ARL4C; SESN3 and ARL4C and RPLP1; even more advantageously the level of expression of the genes of one of the following combinations NME4 and ITPR3 and SESN3 and ARL4C; NME4 and ITPR3 and ARL4C and RPLP1; NME4 and ITPR3 and SESN3 and RPLP1; ITPR3 and SESN3 and ARL4C and RPLP1, and preferably the following combination NME4 and ITPR3 and SESN3 and ARL4C and RPLP1.

Preferably, according to the invention, step a) of the method is carried out by measuring the level of expression of at least one gene (or homologous gene) selected from the NME4, ITPR3, SESN3, ARL4C and RPLP1 genes, or the level of expression of the genes of the following combination NME4 and ITPR3 and SESN3 and ARL4C and RPLP1.

In a first embodiment of the method according to the invention, the level of expression of the gene or genes selected from the group constituted by NME4, ITPR3, SESN3, ARL4C and RPLP1 is measured by measuring the quantity of the protein encoded by said gene in the blood sample from said patient to be tested.

In this case, the level of proteins is preferably measured using methods of detection based on antibodies, such as immunochemistry or Western blot analysis.

In another embodiment of the method according to the invention, the level of expression of the gene or genes is measured by measuring the transcription level of said gene. This level can be measured by measuring the quantity of RNA or cDNA of said gene. In this case, the level of transcribed RNA or cDNA can be measured using methods of detection of nucleic acids such as quantitative PCR, DNA chips, hybridization to labelled probes, or lateral flow immunoassays, in particular using lateral flow strips.

Preferably, in the methods according to the invention, the level of expression of the gene or combination of genes is measured by real-time quantitative PCR (real time quantitative polymerase chain reaction or qPCR) carried out on the RNA transcripts of said gene or on their complementary DNA (cDNA). A qPCR is a PCR in which the amplified DNA is detected in real time while the polymerization reaction proceeds. This detection is based on accumulation of a fluorescent signal.

This technique uses primers (sense and antisense) and a marker, preferably a fluorescent insert of the DNA formed during the cycles of PCR. Advantageously, said primers are specific to the flanking regions of the gene considered.

In the case of the NME4 gene, the flanking regions are situated on chromosome 16 between nucleotides 399665 and 399728 (Assembly December 2013, GRch38/hg38, source UCSC).

In the case of the ITPR3 gene, the flanking regions are situated on chromosome 6 between nucleotides 33696404 and 33696485 (Assembly December 2013, GRch38/hg38 December 2013, source UCSC).

In the case of the SESN3 gene, the flanking regions are situated on chromosome 11 between nucleotides 95166241 and 95166313 (Assembly December 2013, GRch38/hg38, source UCSC).

In the case of the ARL4C gene, the flanking regions are situated on chromosome 4 between nucleotides 234 493 401 and 234 493 502 (Assembly December 2013. GRch38/hg38 December 2013, source UCSC).

In the case of the RPLP1 gene, the flanking regions are situated on chromosome 15 between nucleotides 69455485 and 69455598 (Assembly December 2013, GRch38/hg38 December 2013, source UCSC).

In an advantageous embodiment, the following primers may be used for carrying out qPCR:

```
RNAs derived from the NME4 gene
sense primer:
                                    (SEQ ID NO. 1)
CATGATTGGACACACCGACTC
```

-continued antisense primer:
(SEQ ID NO. 2)
GACGCTGAAGTCACCCCTTAT

RNAs derived from the ITPR3 gene
sense primer:
(SEQ ID NO. 3)
TCCTGGGGAAGAGTTGTACG antisense primer:
(SEQ ID NO. 4)
AGGAGAAAAACAAGCGGTCA RNAs derived from the SESN3 gene
sense primer:
(SEQ ID NO. 5)
TTGCCTTTGTAGTCCTGTGC antisense primer:
(SEQ ID NO. 6)
CATTAGTCCAGTCACGTGCTTC RNAs derived from the ARLC4 gene
sense primer:
(SEQ ID NO. 7)
AAAGCCCTGTGGTGTATCAA antisense primer:
(SEQ ID NO. 8)
GCTTCCTCTGTTGGGTCAGA RNAs derived from the RPLP1 gene
sense primer:
(SEQ ID NO. 9)
TGGGCTTTGGTCTTTTTGAC antisense primer:
(SEQ ID NO. 10)
CAGACCATTTTTGCAGAGCA Using qPCR, it is possible to determine the value of the cycle threshold (Ct) of a gene for the patient to be tested. The Ct ("cycle threshold") is defined as the number of cycles of PCR necessary for the fluorescent signal to exceed the background noise.

The value of Ct obtained may then be normalized with respect to the level of expression of at least one ubiquitous gene expressed as cycle threshold in the same blood sample from the same patient. Said ubiquitous genes are genes that are expressed in all the cells of an organism under normal and pathophysiological conditions. These genes are generally expressed at relatively constant levels.

Preferably, in the methods according to the invention, in step a), besides the level of expression of a marker gene ($Ct_{gene}$) or of each gene of a combination of at least 2 marker genes, the level of expression of at least one ubiquitous gene is measured, said level of expressions being measured as number of cycle(s) (Ct, "cycle threshold") by real-time quantitative PCR (qPCR), and then the level of expression of the marker gene(s) is normalized with respect to the level of expression of the at least one ubiquitous gene according to $$\Delta Ct_{gene}=Ct_{gene}-[(\text{mean value of the})Ct(\text{ubiquitous gene(s)})]$$

to obtain a normalized level of expression $\Delta Ct_{gene}$ for each marker gene the level of expression of which has been measured.

Preferably, in the methods according to the invention, normalization is carried out with respect to the level of expression of two ubiquitous genes, in particular, with respect to the level of expression of the genes GAPDH and B2M. In this case, the normalized level of expression $\Delta Ct_{gene}$ of a marker gene is calculated from:

$$\Delta Ct_{gene}=Ct_{gene}-(Ct_{B2M}+Ct_{GAPDH})/2$$

In the case of the B2M gene, the flanking regions are situated on chromosome 15 between nucleotides 44718721 and 44718792 (Assembly December 2013, GRch38/hg38, source UCSC).

In the case of the GAPDH gene, the flanking regions are situated on chromosome 12 between nucleotides 6534833 and 6536572 (Assembly December 2013, GRch38/hg38, source UCSC).

Primers that are particularly suitable for the B2M and GAPDH e genes may be:

RNAs derived from the B2M gene
sense primer:
(SEQ ID NO. 11)
GCTCAGTAAAGACACAACCATCC antisense primer:
(SEQ ID NO. 12)
CATCTGTGGATTCAGCAAACC RNAs derived from the GAPDH gene
sense primer:
(SEQ ID NO. 13)
ATGGGGAAGGTGAAGGTCG antisense primer:
(SEQ ID NO. 14)
GGGGTCATTGATGGCAACAATA Advantageously, for carrying out qPCR, the primers, their size (preferably between 80 and 150 nucleotides), their melting point (Tm, preferably of 60° C.±1° C.), their percentage of nucleotides G and C (GC %, preferably ~60% at 3'), their 3' and 5' self-complementarity and their stability (preferably less than 4 nucleotides), the ranges of dimensions of the product and the thermodynamic parameters (evolution of the secondary structure according to the Tm of the primers and the concentration of sodium salt) are selected to allow simultaneous detection.

According to a first embodiment, in step a), the level of expression of a single marker gene is measured. In this embodiment, in steps b) and c), the reference thresholds ($S_{ref}$) of a given gene are defined in Table 1 below:

TABLE 1

| Gene | $S_{ref}$ |
|---|---|
| NME4 | 3.1864 |
| ITPR3 | 6.4014 |
| SESN3 | 3.6262 |
| ARL4C | 2.6286 |
| RPLP1 | 6.3748 | a normalized level of expression $\Delta Ct$ of NME4 greater than 3.1864, and/or a normalized level of expression $\Delta Ct$ of ITPR3, SESN3, ARM4C and/or RPLP1 less than 6.4015, 3.6262, 2.6286 and 6.3748 respectively, indicating a long-term survival prognosis, whereas a normalized level of expression $\Delta Ct$ of NME4 less than 3.1864, and/or a normalized level of expression $\Delta Ct$ of ITPR3, SESN3, ARM4C and/or RPLP1 above 6.4015, 3.6262, 2.6286 and 6.3748 respectively, indicating a short-term survival prognosis By "long-term survival" is meant survival of more than 10 months, preferably more than 12 months, even more preferably more than 15 months.

By "short-term survival" is meant survival of less than 6 months, less than 5 months, or less than 3 months.

Moreover, when a patient is assumed to have a long-term survival, this also means that he may be considered eligible for a gemcitabine-based treatment. Conversely, a short-term survival of the patient indicates that a gemcitabine-based treatment will be of little or no benefit to the patient. Another treatment should then be envisaged.

The applicant's investigations (see example 1) on a reference population in fact led to the identification of 5 genes that may be used as markers for a survival prognosis of a patient suffering from pancreatic cancer, but also to the determination, for these 5 genes, of the values for reference thresholds ($S_{ref}$) allowing a comparison to be made.

However, greater accuracy of prognosis may be obtained by measuring a combination of at least two genes. Consequently, according to a second embodiment, in step a), the level of expression of a combination of at least two marker genes is measured and, in steps b), for each marker gene the expression of which has been measured:

i) a value $INDEX_{gene}$ is determined, which is dependent on the normalized level of expression of the gene, defined by:
$INDEX_{gene} = +1*\beta$ coefficient of the gene, if $\Delta Ct_{gene} >$ reference threshold of the gene, and
$INDEX_{gene} = -1*\beta$ coefficient of the gene, if $\Delta Ct_{gene} <$ reference threshold of the gene,
in which the $\beta$ coefficient and the reference threshold of a given gene are as defined in Table 2 below;

TABLE 2

| Gene | $S_{ref}$ | β coefficient |
|---|---|---|
| NME4 | 3.1864 | −1.3207 |
| ITPR3 | 6.4014 | 1.0850 |
| SESN3 | 3.6262 | 1.0301 |
| ARL4C | 2.6286 | 1.3577 |
| RPLP1 | 6.3748 | 1.0101 | ii) for a given patient, a value $INDEX_{patient}$ is determined, which is equal to the sum of the $INDEX_{gene}$s of the genes of the combination, and iii) $INDEX_{patient}$ is compared against a final reference threshold determined beforehand for the combination of genes.

The applicant has thus elaborated a system allowing simplified comparison of the levels of expression of several genes. This comparison system required the development of a coefficient, the beta coefficient (see Table 2 above), for weighting the importance of the different genes in the system.

It follows from the foregoing that the $INDEX_{gene}$s can only take the following values (see Table 3 below):

TABLE 3

| |
|---|
| INDEX NME4 = (+1 or −1) × (−1.3207) = ±1.3207 |
| INDEX ITPR3 = (+1 or −1) × (+1.0850) = ±1.0850 |
| INDEX SESN3 = (+1 or −1) × (+1.0301) = ±1.0301 |
| INDEX ARL4C = (+1 or −1) × (+1.3577) = ±1.3577 |
| INDEX RPLP1 = (+1 or −1) × (+1.0101) = ±1.0101 |

$INDEX_{patient}$ is then calculated, corresponding to the sum of the $INDEX_{gene}$ of the genes of the combination of marker genes the level of expression of which was measured in step a) of the methods according to the invention:

$$INDEX_{patient} = \Sigma INDEX_{gene}$$

This $INDEX_{patient}$ is then compared against a final reference threshold value previously determined by the applicant for each combination of marker genes.

As an example, for the combination of all 5 genes, said final reference threshold value is equal to 1.102.

Thus, on the basis of the final reference threshold value defined for each combination of marker genes, it is possible to establish the survival prognosis for the patient tested.

According to a preferred embodiment of the methods according to the invention, in step a), in a blood sample taken previously from a patient to be tested, by qPCR, the level of expression is measured as cycle threshold ($Ct_{gene}$) of the 5 genes NME4, ITPR3, SESN3, ARL4C and RPLP1 and of the two ubiquitous genes B2M and GAPDH. The normalized level of expression $\Delta Ct_{gene}$ of each of the 5 genes NME4, ITPR3, SESN3, ARL4C and RPLP1 is then calculated from:

$$\Delta Ct_{gene} = Ct_{gene} - (Ct_{B2M} + Ct_{GAPDH})/2$$

An $INDEX_{gene}$ is then calculated for each of the genes from:
$INDEX_{gene} = +1*\beta$ coefficient of the gene, if $\Delta Ct_{gene} >$ reference threshold of the gene, and
$INDEX_{gene} = -1*\beta$ coefficient of the gene, if $\Delta Ct_{gene} <$ reference threshold of the gene
in which the $\beta$ coefficient and the reference threshold of a given gene are as defined in Table 2 below

TABLE 2

| Gene | $S_{ref}$ | β coefficient |
|---|---|---|
| NME4 | 3.1864 | −1.3207 |
| ITPR3 | 6.4014 | 1.0850 |
| SESN3 | 3.6262 | 1.0301 |
| ARL4C | 2.6286 | 1.3577 |
| RPLP1 | 6.3748 | 1.0101 |

$INDEX_{patient}$ is then calculated as:

$$INDEX_{patient} = INDEX_{NME4} + INDEX_{ITPR3} + INDEX_{SESN3} + INDEX_{ARL4C} + INDEX_{RPLP1}.$$

This value of $INDEX_{patient}$ is then compared against the final reference threshold value of the combination of the 5 marker genes, or 1.102.

If a patient has an $INDEX_{patient}$ less than 1.102, he is considered to have a prognosis of long-term survival, and may be considered eligible for a gemcitabine-based treatment. Conversely, if a patient has an $INDEX_{patient}$ greater than 1.102, this indicates that he has a short-term survival prognosis and that a gemcitabine-based treatment will offer little or no benefit. Another treatment should then be envisaged.

The invention also relates to a method for monitoring the efficacy of a treatment for pancreatic cancer by implementing the method according to the invention described above, advantageously at treatment time intervals.

A person skilled in the art will have no difficulty in determining the treatment time intervals at which he wishes to implement the method according to the invention. For example, suitable time intervals are of 1 week, 2 weeks, 1 month, 2 months or 6 months.

The invention also relates to gemcitabine for use in the treatment of pancreatic cancer in a patient who has a prognosis of long-term survival, for example greater than 10 months, advantageously greater than 12 months, even more advantageously greater than 15 months, the prognosis being determined by one of the methods described above.

The invention also relates to gemcitabine for use in the treatment of pancreatic cancer in a patient who has an $INDEX_{patient}$ less than 1.102 calculated according to the preferred embodiment described above.

The invention also relates to gemcitabine for use in the treatment of pancreatic cancer in a patient who has a prognosis of long-term survival, said prognosis of long-term survival being determined by an in-vitro method comprising the following steps:
a) measuring the level of expression of at least one marker gene selected from the group constituted by the NME4, ITPR3, SESN3, ARL4C and RPLP1 genes or homologous genes, in a blood sample taken previously from said patient;
b) comparing the level of expression measured for the marker gene(s) selected in step a) in said patient against a reference threshold;
c) evaluating the survival time for said patient.

The invention also relates to gemcitabine for use in the treatment of pancreatic cancer in a patient who has a prognosis of long-term survival, said prognosis of long-term survival being determined by the in-vitro method as described above, in which, in step a), the level of expression of at least two genes is measured, advantageously of 3, more advantageously of 4, and preferably of 5 genes.

The invention also relates to gemcitabine for use in the treatment of pancreatic cancer in a patient who has a prognosis of long-term survival, said prognosis of long-term survival being determined by an in-vitro method as described above, in which the blood sample is a sample of peripheral whole blood.

The invention also relates to gemcitabine for use in the treatment of pancreatic cancer in a patient who has a prognosis of long-term survival, said prognosis of long-term survival being determined by an in-vitro method as described above, in which the level of expression of the gene or genes is measured by measuring the quantity of the protein or proteins encoded by said gene that is/are present in the blood sample.

The invention also relates to gemcitabine for use in the treatment of pancreatic cancer in a patient who has a prognosis of long-term survival, said prognosis of long-term survival being determined by an in-vitro method as described above, in which the level of expression of the gene or genes is measured from the transcription level of the RNA or cDNA of said gene.

The invention also relates to gemcitabine for use in the treatment of pancreatic cancer in a patient who has a prognosis of long-term survival, said prognosis of long-term survival being determined by the in-vitro method as described above, in which, in step a), besides the level of expression of a marker gene ($Ct_{gene}$) or of each gene of a combination of at least 2 marker genes, the level of expression of at least one ubiquitous gene is measured, said levels of expression being measured as number of cycle(s) (Ct, "cycle threshold") by real-time quantitative PCR (qPCR), then the level of expression of the marker gene(s) is normalized with respect to the level of expression of the at least one ubiquitous gene according to $$\Delta Ct_{gene} = Ct_{gene} - [(\text{mean value of the}) Ct(\text{ubiquitous gene(s)})]$$

to obtain a normalized level of expression $\Delta Ct_{gene}$ for each marker gene the level of expression of which has been measured.

The invention also relates to gemcitabine for use in the treatment of pancreatic cancer in a patient who has a prognosis of long-term survival, said prognosis of long-term survival being determined by the in-vitro method as described above, in which the normalized level of expression $\Delta Ct$ of a marker gene or of each gene of a combination of at least two marker genes is normalized with respect to two ubiquitous genes B2M and GAPDH.

The invention also relates to gemcitabine for use in the treatment of pancreatic cancer in a patient who has a prognosis of long-term survival, said prognosis of long-term survival being determined by the in-vitro method as described above, in which, in step a), the level of expression of a single marker gene is measured and, in steps b) and c), the reference thresholds ($S_{ref}$) of a given gene are:

| Gene | $S_{ref}$ |
|---|---|
| NME4 | 3.1864 |
| ITPR3 | 6.4014 |
| SESN3 | 3.6262 |
| ARL4C | 2.6286 |
| RPLP1 | 6.3748 | a normalized level of expression $\Delta Ct$ of NME4 greater than 3.1864 and/or
a normalized level of expression $\Delta Ct$ of ITPR3, SESN3, ARL4C and/or RPLP1 less than 6.4015, 3.6262, 2.6286 and 6.3748 respectively indicating a prognosis of long-term survival.

The invention also relates to gemcitabine for use in the treatment of pancreatic cancer in a patient who has a prognosis of long-term survival, said prognosis of long-term survival being determined by the in-vitro method as described above, in which, in step a), the level of expression of a combination of at least two marker genes is measured and, in steps b), for each gene the expression of which has been measured
i) a value $INDEX_{gene}$ is determined, which is dependent on the normalized level of expression of the gene, defined by:
$INDEX_{gene} = +1*\beta$ coefficient of the gene, if $\Delta Ct_{gene}$ >reference threshold of the gene, and
$INDEX_{gene} = -1*\beta$ coefficient of the gene, if $\Delta Ct_{gene}$ <reference threshold of the gene, and
in which the $\beta$ coefficient and the reference threshold ($S_{ref}$) of a given gene are as defined below

| Gene | $S_{ref}$ | $\beta$ coefficient |
|---|---|---|
| NME4 | 3.1864 | −1.3207 |
| ITPR3 | 6.4014 | 1.0850 |
| SESN3 | 3.6262 | 1.0301 |
| ARL4C | 2.6286 | 1.3577 |
| RPLP1 | 6.3748 | 1.0101 | ii) a value $INDEX_{patient}$, equal to the sum of the $INDEX_{gene}$ of the genes of the combination, is determined for a given patient, and
iii) $INDEX_{patient}$ is compared against a final reference threshold previously determined for the combination of genes.

The invention also relates to gemcitabine for use in the treatment of pancreatic cancer in a patient who has a prognosis of long-term survival, said prognosis of long-term survival being determined by the in-vitro method as described above, in which the level of expression of the 5 marker genes is measured, the final reference threshold being 1.102, an INDEX$_{patient}$ less than 1.102 indicating a prognosis of long-term survival.

The invention also relates to gemcitabine for use in the treatment of pancreatic cancer in a patient who has an INDEX$_{patient}$ less than 1.102, INDEX$_{patient}$ being determined by the method according to the invention, in which the level of expression of the 5 marker genes is measured, the final reference threshold being 1.102, an INDEX$_{patient}$ less than 1.102 indicating a prognosis of long-term survival.

The invention also relates to gemcitabine for use in the treatment of pancreatic cancer in a patient who has an INDEX$_{patient}$ less than 1.102, INDEX$_{patient}$ being determined by an in-vitro method comprising the following steps:

a) measuring the level of expression of a combination of the five marker genes NME4, ITPR3, SESN3, ARL4C and RPLP1 and of two ubiquitous genes B2M and GADPH in a blood sample taken previously from said patient, the level of expression of the genes corresponding to the transcription level of the RNA or cDNA of said genes, measured as number of cycle(s) (Ct, "cycle threshold") by real-time quantitative PCR (qPCR), the level of expression of the five marker genes then being normalized with respect to the level of expression of the ubiquitous genes according to $$\Delta Ct_{gene} = Ct_{gene} - [\text{mean value of the } Ct_{ubiquitous\ genes}]$$

to obtain a normalized level of expression $\Delta Ct_{gene}$ for each of the five marker genes, b) comparing the level of expression measured for the marker genes selected in step a) in said patient and for each gene the expression of which has been measured:
  i) a value INDEX$_{gene}$ is determined, which is dependent on the normalized level of expression of the gene, defined by:
    INDEX$_{gene}$=+1*β coefficient of the gene, if $\Delta Ct_{gene}$>reference threshold of the gene, and
    INDEX$_{gene}$=−1*β coefficient of the gene, if $\Delta Ct_{gene}$<reference threshold of the gene, and
  in which the β coefficient and the reference threshold (S$_{ref}$) of a given gene are as defined below

| Gene  | S$_{ref}$ | β coefficient |
|-------|--------|---------------|
| NME4  | 3.1864 | −1.3207       |
| ITPR3 | 6.4014 | 1.0850        |
| SESN3 | 3.6262 | 1.0301        |
| ARL4C | 2.6286 | 1.3577        |
| RPLP1 | 6.3748 | 1.0101        | ii) a value INDEX$_{patient}$, equal to the sum of the INDEX$_{gene}$ of the genes of the combination, is determined for a given patient, and
  iii) INDEX$_{patient}$ is compared against the final reference threshold of 1.102;

c) evaluating the survival time for said patient, an INDEX$_{patient}$ less than 1.102 indicating a prognosis of long-term survival.

The present invention further relates to a DNA chip having, on its surfaces, nucleic acids capable of hybridizing to at least one of the genes selected from the group constituted by NME4, ITPR3, SESN3, ARL4C and RPLP1, preferably at least 2, 3 or 4 genes and, more preferably, for detecting the level of expression of all 5 genes, optionally with nucleic acids specific to at least one ubiquitous gene, preferably two ubiquitous genes, even more preferably nucleic acids specific to the ubiquitous genes B2M and GAPDH.

The present invention also relates to a kit for determining the prognosis of pancreatic cancer in a patient, comprising means for detecting the level of expression of at least two genes selected from the group constituted by NME4, ITPR3, SESN3, ARL4C and RPLP1, preferably at least 2, 3 or 4 genes and, more preferably, for detecting the level of expression of all 5 genes.

The means for detecting the level of expression may be for example a DNA chip according to the invention, a set of primers and a reporter such as fluorescent agents, labelled hydrolysis probes, molecular beacons, hybridization probes, and antibodies.

Preferably, the kit according to the invention may comprise means for detecting the level of expression of a combination of genes selected from the group constituted by NME4, ITPR3, SESN3, ARL4C and RPLP1.

More preferably, the kit according to the invention may comprise means for detecting all the combinations of genes mentioned above, preferably at least 2, 3 or 4 genes and, more preferably, means for detecting the combination of all 5 genes.

The kit may further comprise instructions for use in the in-vitro method according to the invention.

Finally, the invention also relates to the use of at least one gene selected from the group constituted by NME4, ITPR3, SESN3, ARL4C and RPLP1, for prognosis of pancreatic cancer, in particular during gemcitabine-based treatment.

Preferably, the invention relates to the use of at least one of the combinations of 2 to 5 genes selected from the group constituted by NME4, ITPR3, SESN3, ARL4C and RPLP1 and preferably the combination of 3 genes, more preferably of 4 genes, even more preferably of all 5 genes, for prognosis of pancreatic cancer, in particular during gemcitabine-based treatment.

The invention also relates to the use of at least one gene selected from the group constituted by the genes NME4, ITPR3, SESN3, ARL4C and RPLP1 or homologous genes, preferably at least 2, 3 or 4 genes and, more preferably, all 5 genes for prognosis of pancreatic cancer in a patient, as well as the use of at least one gene selected from the group constituted by the genes NME4, ITPR3, SESN3, ARL4C and RPLP1 or homologous genes, preferably at least 2, 3 or 4 genes and, more preferably, all 5 genes for monitoring the efficacy of a treatment of pancreatic cancer, advantageously of treatment with gemcitabine, in a patient.

The present invention will be better understood and other advantages and features will become apparent on reading the following examples and the appended drawings in which:

FIG. 1A shows the distribution of certain statistical values of the Mantel-Cox test as a function of their ΔCt value. In order to determine the cut-point between 2 groups, the maximum value obtained by an individual for the Mantel-Cox test statistic is determined and the graph is read to determine the value of the reference threshold (S$_{ref}$) of 3.1864.

FIG. 1B shows the survival curves calculated by the Kaplan-Meier method for the 2 survival groups at the end of the calculation of the threshold value. The group shown in black is the set of individuals the ΔCt value of which is less than the threshold value (S$_{ref}$) and the group shown in grey is the set of individuals the ΔCt value of which is greater than the threshold value (S$_{ref}$). Here, the group with long-term survival is the black group. The p-value of the log-rank test is given at the top of the graph: P=9.59×10$^{−5}$.

FIG. 2A shows the distribution of certain statistical values of the Mantel-Cox test as a function of their ΔCt value. In order to determine the cut-point between 2 groups, the maximum value obtained by an individual for the Mantel-Cox test statistic is determined, and by reading the graph it is possible to determine the value of the reference threshold ($S_{ref}$) of 6.4015.

FIG. 2B shows the survival curves calculated by the Kaplan-Meier method for the 2 survival groups at the end of the calculation of the threshold value. The group shown in black is the set of individuals the ΔCt value of which is less than the threshold value ($S_{ref}$) and the group shown in grey is the set of individuals the ΔCt value of which is greater than the threshold value ($S_{ref}$). Here, the group with long-term survival is the grey group. The p-value of the log-rank test is given at the top of the graph: P=0.000219.

FIG. 3A shows the distribution of certain statistical values of the Mantel-Cox test as a function of their ΔCt value. In order to determine the cut-point between 2 groups, the maximum value obtained by an individual for the Mantel-Cox test statistic is determined, and by reading the graph it is possible to determine the value of the reference threshold ($S_{ref}$) of 3.6262.

FIG. 3B shows the survival curves calculated by the Kaplan-Meier method for the 2 survival groups at the end of the calculation of the threshold value. The group shown in black is the set of individuals the ΔCt value of which is less than the threshold value ($S_{ref}$) and the group shown in grey is the set of individuals the ΔCt value of which is greater than the threshold value ($S_{ref}$). Here, the group with long-term survival is the grey group. The p-value of the log-rank test is given at the top of the graph: P=0.000331.

FIG. 4A shows the distribution of certain statistical values of the Mantel-Cox test as a function of their ΔCt value. In order to determine the cut-point between 2 groups, the maximum value obtained by an individual for the Mantel-Cox test statistic is determined, and by reading the graph it is possible to determine the value of the reference threshold ($S_{ref}$) of 2.6286.

FIG. 4B shows the survival curves calculated by the Kaplan-Meier method for the 2 survival groups at the end of the calculation of the threshold value. The group shown in black is the set of individuals the ΔCt value of which is less than the threshold value ($S_{ref}$) and the group shown in grey is the set of individuals the ΔCt value of which is greater than the threshold value ($S_{ref}$). Here, the group with long-term survival is the grey group. The p-value of the log-rank test is given at the top of the graph: P=0.000472.

FIG. 5A shows the distribution of certain statistical values of the Mantel-Cox test as a function of their ΔCt value. In order to determine the cut-point between 2 groups, the maximum value obtained by an individual for the Mantel-Cox test statistic is determined, and by reading the graph it is possible to determine the value of the reference threshold ($S_{ref}$) of 6.3748.

FIG. 5B shows the survival curves calculated by the Kaplan-Meier method for the 2 survival groups at the end of the calculation of the threshold value. The group shown in black is the set of individuals the ΔCt value of which is less than the threshold value ($S_{ref}$) and the group shown in grey is the set of individuals the ΔCt value of which is greater than the threshold value ($S_{ref}$). Here, the group with long-term survival is the grey group. The p-value of the log-rank test is given at the top of the graph: P=0.00053.

FIG. 6A shows the distribution of certain statistical values of the Mantel-Cox test as a function of their ΔCt value. In order to determine the cut-point between 2 groups, the maximum value obtained by an individual for the Mantel-Cox test statistic is determined, and by reading the graph it is possible to determine the value of the reference threshold ($S_{ref}$) of 1.102.

FIG. 6B shows the survival curves calculated by the Kaplan-Meier method for the 2 survival groups at the end of the calculation of the threshold value. The group shown in black is the set of individuals the ΔCt value of which is less than the threshold value ($S_{ref}$) and the group shown in grey is the set of individuals the ΔCt value of which is greater than the threshold value ($S_{ref}$). Here, the group with long-term survival is the grey group. The p-value of the log-rank test is given at the top of the graph: $P=1.01\times10^{-08}$.

Figure 1:
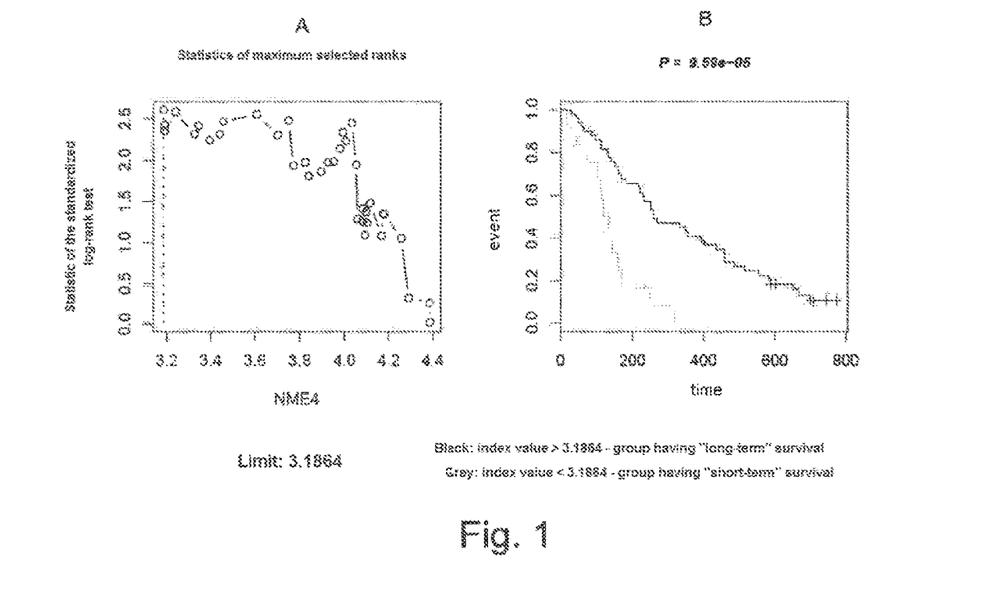
FIG. 1 shows the results obtained by the inventors in determination of the reference threshold for the NME4 gene.
Figure 2:
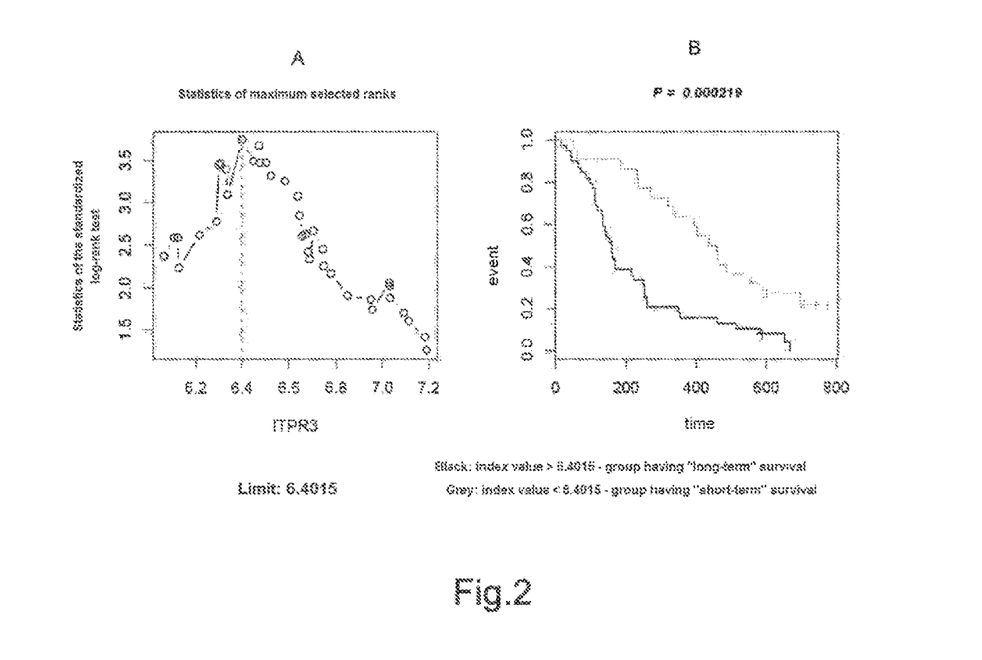
FIG. 2 shows the results obtained by the inventors in determination of the reference threshold for the ITPR3 gene.
Figure 3:
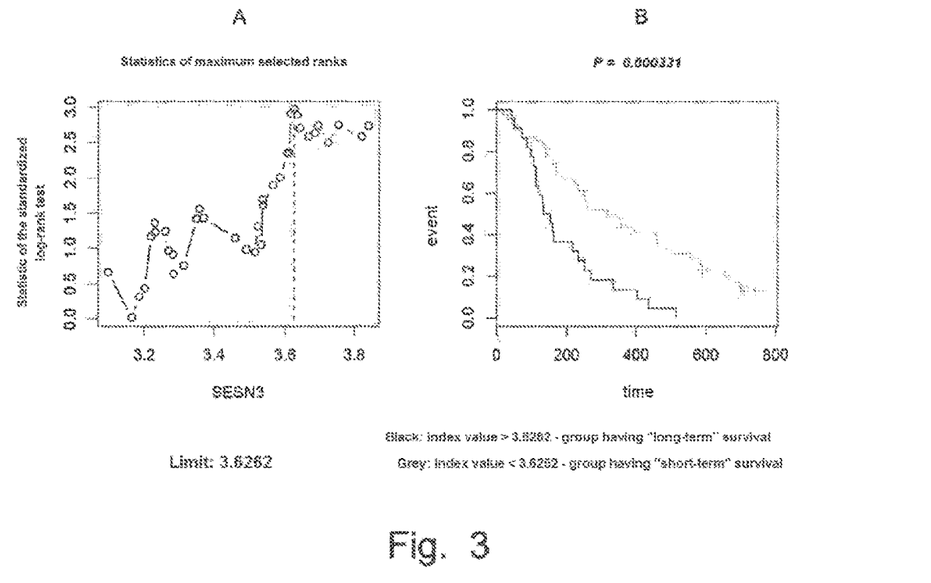
FIG. 3 shows the results obtained by the inventors in determination of the reference threshold for the SESN3 gene.
Figure 4:
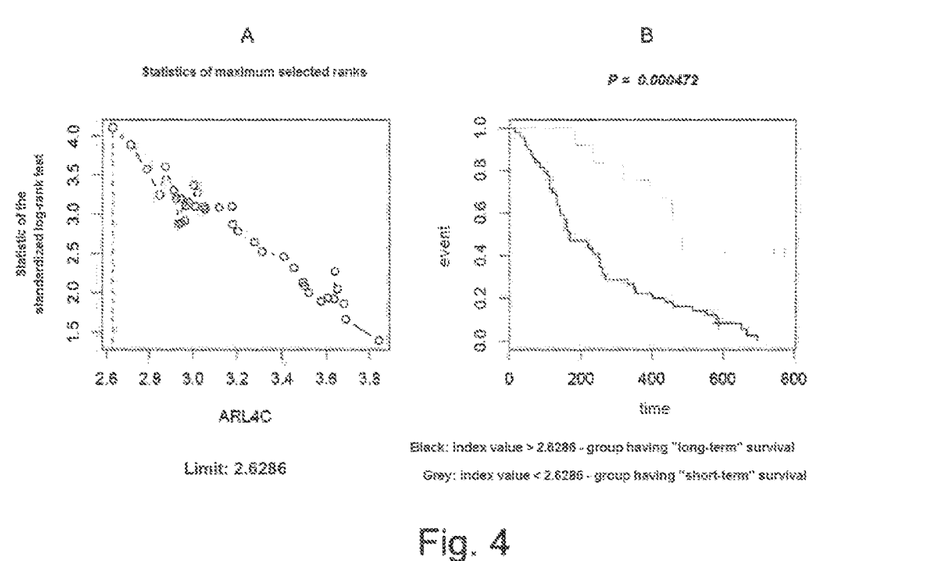
FIG. 4 shows the results obtained by the inventors in determination of the reference threshold for the ARL4C gene.
Figure 5:
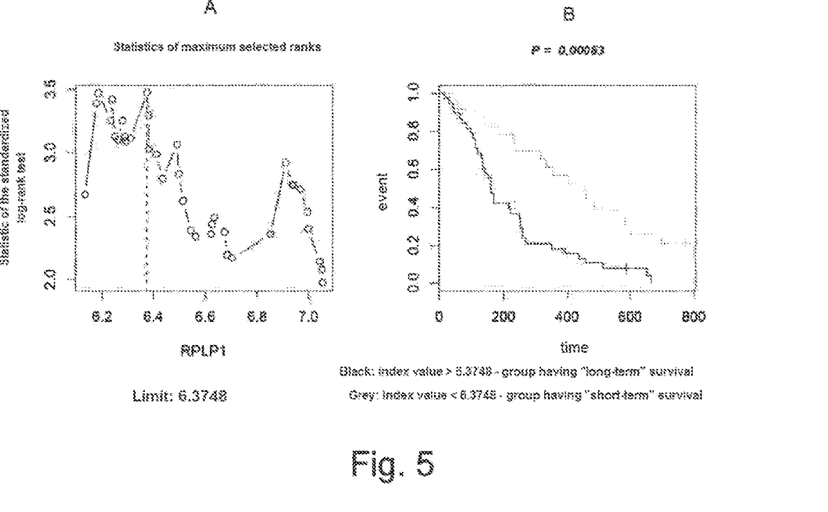
FIG. 5 shows the results obtained by the inventors in determination of the reference threshold for the RPLP1 gene.
Figure 6:
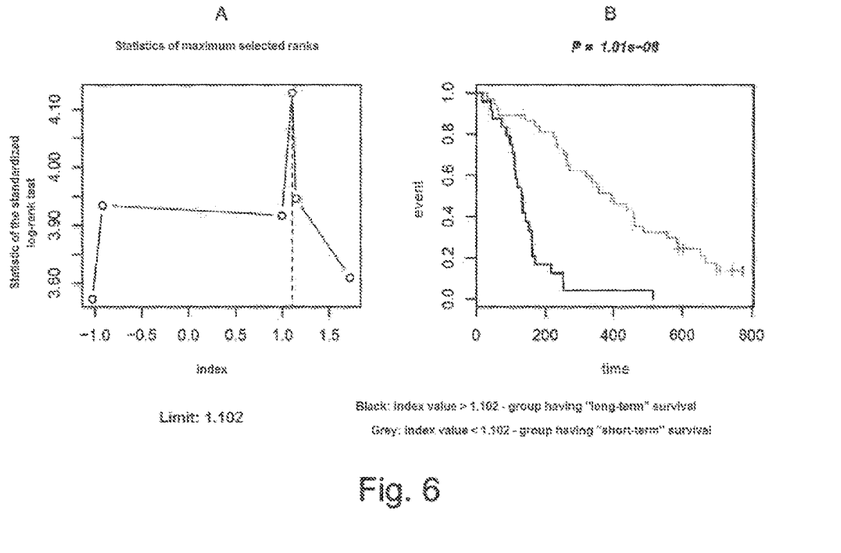
FIG. 6 shows the results obtained by the inventors in determination of the final reference threshold for the combination of all 5 genes NME4, ITPR3, SESN3, ARL4C, RPLP1.

EXAMPLE 1: IDENTIFICATION OF A SET OF GENES FOR THE PROGNOSIS OF PANCREATIC CANCER 1.1 Preparation of the RNA Samples of whole blood from 61 patients, taken before treatment, packaged in PAXgene tubes in dry ice (supplier: LabConnect, United States) were received and stored at −80° C. They were designated "week 0".

The total RNA was extracted from the 61 samples of whole blood and designated "week 0". Analysis of the transcriptome (search for biomarkers) was only carried out on these "week 0" samples.

The 61 samples of RNA were analysed in order to determine their quality. The integrity of the RNA was checked with the Bioanalyzer 2100 (Agilent Technologies, Palo Alto, United States) using the "Eukaryotic total RNA 6000 Nano Chip" from Agilent Technologies). The quantity of RNA was checked using a NanoDrop ND-1000 spectrophotometer (THERMO Scientific). The purified RNAs were stored at −80° C.

One sample was eliminated from the study on account of the poor quality of the RNA (RNA Integrity Number <8).

60 samples of whole blood RNA, which correspond to reference blood samples, were extracted from the blood previously collected (blood sampling tubes PAXgene, BD) using PAXgene Blood RNA Kit V.2 (PreAnalitix) according to the manufacturer's recommendations.

Digital gene expression (DGE) experiments were carried out for selecting a set of putative biomarkers.

The biomarkers were validated using a COBAS platform (LC480, Roche Diagnostics) and the appropriate biostatistical approaches were used for filtering the best biomarkers.

| Subject No. | Treatment | Deaths | Survival (days) | Survival (months) |
|---|---|---|---|---|
| 110 | Gemcitabine | YES | 183 | 6.0 |
| 111 | Gemcitabine | NO | 744 | 24.4 |
| 112 | Gemcitabine | YES | 112 | 3.7 |
| 113 | Gemcitabine | NO | 589 | 19.4 |
| 207 | Gemcitabine | YES | 98 | 3.2 |
| 208 | Gemcitabine | YES | 87 | 2.9 |
| 211 | Gemcitabine | YES | 160 | 5.3 |
| 508 | Gemcitabine | YES | 253 | 8.3 |
| 805 | Gemcitabine | YES | 654 | 21.5 |
| 1104 | Gemcitabine | YES | 402 | 13.2 |
| 1203 | Gemcitabine | YES | 252 | 8.3 |
| 1612 | Gemcitabine | YES | 47 | 1.5 |
| 1613 | Gemcitabine | YES | 73 | 2.4 |
| 2009 | Gemcitabine | YES | 113 | 3.7 |
| 2403 | Gemcitabine | YES | 222 | 7.3 |
| 2703 | Gemcitabine | YES | 61 | 2.0 |
| 2704 | Gemcitabine | YES | 134 | 4.4 |
| 3110 | Gemcitabine | YES | 260 | 8.5 |
| 3111 | Gemcitabine | YES | 144 | 4.7 |
| 3308 | Gemcitabine | YES | 217 | 7.1 |
| 3309 | Gemcitabine | YES | 112 | 3.7 |
| 3407 | Gemcitabine | YES | 171 | 5.6 |
| 3408 | Gemcitabine | YES | 350 | 11.5 |
| 3706 | Gemcitabine | NO | 774 | 25.4 |
| 4407 | Gemcitabine | YES | 135 | 4.4 |
| 4409 | Gemcitabine | YES | 515 | 16.9 |
| 4410 | Gemcitabine | NO | 708 | 23.3 |
| 4411 | Gemcitabine | YES | 105 | 3.4 |
| 4414 | Gemcitabine | YES | 437 | 14.4 |
| 4415 | Gemcitabine | YES | 17 | 0.6 |
| 4503 | Gemcitabine | NO | 700 | 23.0 |
| 4702 | Gemcitabine | YES | 31 | 1.0 |
| 4902 | Gemcitabine | YES | 161 | 5.3 |
| 4903 | Gemcitabine | NO | 602 | 19.8 |
| 5008 | Gemcitabine | YES | 588 | 19.3 |
| 5201 | Gemcitabine | YES | 584 | 19.2 |
| 5202 | Gemcitabine | YES | 43 | 1.4 |
| 5331 | Gemcitabine | YES | 699 | 23.0 |
| 5336 | Gemcitabine | YES | 486 | 16.0 |
| 5339 | Gemcitabine | YES | 65 | 2.1 |
| 5340 | Gemcitabine | YES | 356 | 11.7 |
| 5341 | Gemcitabine | YES | 120 | 3.9 |
| 5342 | Gemcitabine | YES | 393 | 12.9 |
| 5344 | Gemcitabine | YES | 667 | 21.9 |
| 5345 | Gemcitabine | YES | 251 | 8.2 |
| 5346 | Gemcitabine | YES | 163 | 5.4 |
| 5703 | Gemcitabine | YES | 261 | 8.6 |
| 5901 | Gemcitabine | YES | 555 | 18.2 |
| 6201 | Gemcitabine | YES | 52 | 1.7 |
| 6303 | Gemcitabine | YES | 269 | 8.8 |
| 8001 | Gemcitabine | YES | 458 | 15.0 |
| 8003 | Gemcitabine | YES | 335 | 11.0 |
| 8106 | Gemcitabine | YES | 461 | 15.1 |
| 8901 | Gemcitabine | YES | 460 | 15.1 |
| 9312 | Gemcitabine | YES | 141 | 4.6 |
| 9508 | Gemcitabine | YES | 169 | 5.6 |
| 9509 | Gemcitabine | YES | 318 | 10.4 |
| 9901 | Gemcitabine | YES | 153 | 5.0 |
| 10303 | Gemcitabine | YES | 131 | 4.3 |
| 10304 | Gemcitabine | YES | 234 | 7.7 |
| 11207 | Gemcitabine | YES | 231 | 7.6 |

1.2. Construction of the DGE Library and Beacon-Gene Mapping

The RNA samples were divided into 2 groups:

M4: corresponding to the patients who received gemcitabine after collection of the reference blood samples, and who died before month 4;

M15: corresponding to the patients who received gemcitabine after collection of the reference blood samples, and were alive after month 15.

For each group, equimolar quantities of each sample of total RNA from the patients were mixed in order to constitute a pool of total RNA.

6 libraries of the DGE type (technique repeated three times for each group) were constructed from said pools.

The libraries were constructed with the kit provided for this purpose by the company Illumina (DGE Tag profiling kit) according to the manufacturers protocol (version 2.1B), using 2 µg of total RNA.

The sequencing and the subsequent analyses were carried out using the Pipeline device from Illumina.

The MGX platform (Montpellier, France) was used.

The data of each DGE library were analysed with the BIOTAG software (Acobiom, Montpellier, France) for detecting and counting beacons, and assessment of the quality of the DGE libraries (Piquemal et al., 2002).

1.3. Labelling and Selection of Beacons

A database compiling sequences of *Homo sapiens* and related data was generated starting from sequences obtained from the UniGene database (Built#232, March 2012, NCBI).

For each sequence in the database, the expected DGE beacon (canonical beacon) situated upstream of the NlaIII restriction site (CATG) nearest the 3' end of the sequence (R1), as well as the putative beacons situated at internal positions (labelled R2, R3 and R4 starting from the 3' end of the transcript), were extracted (Piquemal et al., 2002).

Experimental beacons obtained from the DGE libraries were paired and labelled (exact correspondences for the 17 bp) using this collection of virtual beacons. A correspondence for each experimental beacon with the virtual canonical beacons (R1) was sought first. Then, the experimental beacons not paired with the beacons R2, then with R3 and R4 were labelled.

The DGE experiments were analysed using the edgeR method (version 2.6.9, Bioconductor). The genes analysed were selected as a function of (1) mathematical filters having the largest factor of differential variation ("differential Fold Change", >1.5), The rate of false positives (FDR) is an adjusted p-value (here FDR<10% is assumed), which is calculated according to the type 1 error ($\alpha$=5%) reported in the general considerations. (J.R. Statist. Soc. B, 2010, Discovering the false discovery rate, Y Benjamini)

(2) biological filters with the application of targeted genes in specific processes and known metabolic pathways.

1.4. Synthesis of cDNA for qPCR

Reverse transcription was carried out for each of the 60 samples of RNAs in 20 µl of final reaction volume with 300 ng of total RNA using 200 units of the enzyme SuperScript II (M-MLV type TA, Invitrogen) and 250 ng of random primers according to the manufacturer's instructions (25° C., 10 min, 42° C., 50 min, 70° C. 15 min), on the same day with the same pipette and the same manipulator.

1.5. qPCR

The targeted genes were validated by qPCR on a platform from Roche Diagnostics.

The qPCR experiments were carried out using a LightCycler® 480 DNA SYBR Green Master mix (Roche Diagnostics) on a Roche Diagnostics LightCycler480® instrument according to the manufacturer's instructions.

For the assays with SYBR Green, the reaction mixture was prepared as follows in a final volume of 10 µl: 5 µl of LightCycler 480 DNA SYBR Green Master 2X (Roche), 4 µl of primer pairs at 50 µM (Eurogentec), 1 µl of cDNA matrix (1/15 final dilution).

The PCR programme consists of a first step of preincubation at 95° C. for 10 min followed by 45 cycles of PCR (95°C. for 10 s, 63° C. for 15 s and 72° C. for 15 s).

In order to distinguish the specific products from the non-specific products and the primer dimers, melting was obtained by gradually increasing the temperature from 65 to 97° C.

TABLE 4 primers corresponding to the 5 biomarkers used for qPCR as well as the 2 reference genes (*ubiquitous genes).

| Bio-marker | Sense primer | Antisense primer |
|---|---|---|
| NME4 | CATGATTGGACACACCGACTC (SEQ ID NO. 1) | GACGCTGAAGTCACCCCTT AT (SEQ ID NO. 2) |
| ITPR3 | TCCTGGGGAAGAGTTGTACG (SEQ ID NO. 3) | AGGAGAAAAACAAGCGGTC A (SEQ ID NO. 4) |
| SESN3 | TTGCCTTTGTAGTCCTGTGC (SEQ ID NO. 5) | CATTAGTCCAGTCACGTGC TTC (SEQ ID NO. 6) |
| ARL4C | AAAGCCCTGTGGTGTATCAA (SEQ ID NO. 7) | GCTTCCTCTGTTGGGTCAG A (SEQ ID NO. 8) |
| RPLP-1 | TGGGCTTTGGTCTTTTTGAC (SEQ ID NO. 9) | CAGACCATTTTTGCAGAGC A (SEQ ID NO. 10) |
| B2M* | GCTCAGTAAAGACACAACCA TCC (SEQ ID NO. 11) | CATCTGTGGATTCAGCAAA CC (SEQ ID NO. 12) |
| GAPDH* | ATGGGGAAGGTGAAGGTCG (SEQ ID NO. 13) | GGGGTCATTGATGGCAACA ATA (SEQ ID NO. 14) |

The data from qPCR were analysed using the Delta.Ct (ΔCt) method (Livak and Schmittgen, 2001). For all the target genes, the ΔCt values were determined by application of the formula $$\Delta Ct = Ct(\text{gene}) - [Ct(\text{B2M}) + Ct(\text{GAPDH})]/2$$

The two ubiquitous genes are:
B2M (NM_009735, beta-2 microglobulin from *Mus musculus*, mRNA) and
GAPDH (NM_002046, glyceraldehyde-3-phosphate dehydrogenase, transcription variant 1, mRNA+ NM_001256799 glyceraldehyde-3-phosphate dehydrogenase from *Homo sapiens*, transcription variant 2, mRNA).

1.6. Results
Identification of the Genetic Fingerprint

Using the DGE method, the transcriptome profiles of patients' whole blood were obtained and 169 genes were selected with the edgeR method as described in section 1.3.

In a qPCR assay, a positive reaction is detected by an accumulation of a fluorescent signal.

With Ct defined as the number of PCR cycles necessary for the fluorescent signal to exceed the background noise, the Ct value is inversely proportional to the quantity of target nucleic acid in the sample. Thus, the lower the Ct value, the greater the quantity of target nucleic acid in the sample.

An additional pharmacogenomic study was also carried out. Samples of the RNA from blood from 61 patients were taken before any treatment, and they were analysed by RT-PCR.

A genetic pro-metastatic fingerprint present in 65% of the patients, highly predictive of the overall survival, and, moreover, interacting with the type of treatment, was demonstrated. The patients treated with gemcitabine who have the genetic pro-metastatic fingerprint have a low overall survival rate (OS) (5.0 months).

The NME4, ITPR3, SESN3, ARL4C and RPLP1 genes were selected by the inventors from the 169 genes, in agreement with the multifactorial nature of this indication.

| Name | Description | Ensembl identifier | GenBank identifier (example of mRNA) |
|---|---|---|---|
| NME4 | *Homo sapiens* NME/NM23 nucleoside diphosphate kinase 4 | ENSG00000103202 | ENSDG00000103202 NM_001286433.1 NM_001286439.1 NM_001286440.1 NM_001286438.1 NM_001286436.1 NM_005009.2 NM_001286435.1 |
| ITPR3 | inositol 1,4,5-triphosphate receptor, type 3 | ENSG00000096433 | ENSG00000096433 NM_002224.3 XM_011514576.1 XM_011514577.1 |
| SESN3 | sestrin 3 | ENSG00000149212 | ENSG00000149212 NM_001271594.1 NM_144665.3 |
| ARL4C | ADP-ribosylation factor like 4C | ENSG00000188042 | NM_005737 AJ579850* AJ57985* NM_001282431.1 NM_005737.3 |
| RPLP1 | Large ribosomal protein P1 | ENSG00000137818 | NM_001003 NM_213725 NM_001003.2 NM_213725.1 |
| GAPDH | glyceraldehyde-3-phosphate dehydrogenase | ENSG00000111640 | NM_002046 NM_001256799 |
| B2M | beta-2 microglobulin | ENSG00000166710 | NM_009735 |

*Splice variants of the transcript of the ARL7 gene (*Homo sapiens* mRNA for ADP ribosylation factor-like protein 7 (ARL7 gene), splice variant 1 (ENSG00000188042), known to be homonyms of ARL4C.

The identification of the genetic fingerprint described here opens up a new route to personalized therapy in this indication.

The genetic pro-metastatic fingerprint, based on a specific value of Delta.Ct (ΔCt), can usually be determined by RT-PCT starting from RNA of blood samples. The ΔCt value illustrating the level of expression of a given gene in a given patient is obtained by RT-PCR amplification of the given gene and after normalizing with respect to the reference genes (B2M, GAPDH). The lower the ΔCt value, the greater the level of expression of the gene.

The patients who have a high survival prognosis and/or are eligible for treatment with gemcitabine have a specific INDEX value.

Determination of the INDEX Values

More precisely, each gene identified (NME4, ITPR3, SESN3, ARL4C and RPLP1) was evaluated for its prognostic value for overall survival on a standard population of patients with pancreatic cancer (reference population), before said patients received treatment (see point 1.1).

A threshold value of ΔCT was defined by qPCR for said reference population and for the 5 genes identified (NME4, ITPR3, SESN3, ARL4C and RPLP1).

Then, for the 5 genes identified (NME4, ITPR3, SESN3, ARL4C and RPLP1), a Mantel-Cox model (or Log-Rank test, "logarithmic test by rank") tested the difference in survival between long-term survival and short-term survival, and established a "reference threshold" ($S_{ref}$) and a "beta coefficient" for each gene identified. This Log-rank test makes it possible to compare two groups the survival curves of which have been calculated by the Kaplan Meier method. It tests the null hypothesis H0 of equality of the survival functions in the two groups considered. Under H0, as the risk of death is the same at a given time Ti between the two groups, an identical proportion of deaths in the latter is expected (Bland & Altman, 2004).

Table 2 below shows the values of the reference threshold ($S_{ref}$) and of the beta coefficient obtained for the 5 genes NME4, ITPR3, SESN3, ARL4C and RPLP1, on the reference population.

TABLE 2 threshold and beta coefficient (β coefficient) for the 5 genes identified

| Name | $S_{ref}$ | β coefficient |
|---|---|---|
| NME4 | 3.1864 | −1.3207 |
| ITPR3 | 6.4014 | 1.0850 |
| SESN3 | 3.6262 | 1.0301 |
| ARL4C | 2.6286 | 1.3577 |
| RPLP1 | 6.3748 | 1.0101 |

A normalized expression level ΔCt of NME4 greater than 3.1864, and/or
  normalized expression level ΔCt of ITPR3, SESN3, ARM4C and/or RPLP1 less than 6.4015, 3.6262, 2.6286 and 6.3748 respectively, indicates a prognosis of long-term survival, whereas
a normalized expression level ΔCt of NME4 less than 3.1864, and/or
a normalized expression level ΔCt of ITPR3, SESN3, ARM4C and/or RPLP1 greater than 6.4015, 3.6262, 2.6286 and 6.3748 respectively, indicates a short-term survival prognosis.

The prognosis may be refined by taking a combination of the 5 genes in Table 2.

The ΔCT value obtained is then corrected as a variable that may take two values:
  +1 if the ΔCT value of the samples is strictly greater than the value of $S_{ref}$ defined for the gene considered;
  −1 if the ΔCT value of the samples is strictly less than the value of $S_{ref}$ defined for the gene considered.

This then makes it possible to define, for each gene considered, an INDEX value that is calculated according to: INDEX=(+1 or −1)×(β coefficient).

Thus, for the genes considered, the INDEX calculated on the reference population of patients suffering from pancreatic cancer may take the values given in Table 3 below:

TABLE 3

INDEX NME4 = (+1 or −1) × (−1.3207) = ±1.3207
INDEX ITPR3 = (+1 or −1) × (+1.0850) = ±1.0850
INDEX SESN3 = (+1 or −1) × (+1.0301) = ±1.0301
INDEX ARL4C = (+1 or −1) × (+1.3577) = ±1.3577
INDEX RPLP1 = (+1 or −1) × (+1.0101) = ±1.0101

It is the INDEX of the combination of genes retained for assessing the survival prognosis for the patient that will then allow the prognosis to be established.

The Mantel-Cox model (or Log-Rank test), taking into account the calculated INDEX values, made it possible to determine a "final reference threshold" for each of the combinations, which will allow the survival prognosis for the patient tested to be established.

The value of the final reference threshold for the combination of all 5 genes considered is equal to 1.102.

On the basis of the final reference threshold value defined for each gene or for each combination, it is possible to establish the survival prognosis for the patient tested:
  if $INDEX_{patient}$ calculated for the patient tested is less than the value of the final reference threshold, the prognosis is long-term survival and
  if $INDEX_{patient}$ calculated for the patient tested is greater than the value of the final reference threshold, the prognosis is short-term survival.

The invention claimed is:

1. A method for treating a patient suffering from pancreatic cancer, comprising the following steps:

a) measuring the level of expression of each gene ($Ct_{gene}$) of a combination of at least NME4 and ARL4C marker genes and optionally ITPR3, SESN3, and/or RPLP1 marker gene(s) and the level of expression of two ubiquitous B2M and GAPDH genes in a blood sample taken previously from said patient, said levels of expression being measured from the transcription level of the RNA or cDNA of said gene as number of cycle(s) (Ct, "cycle threshold") by real-time quantitative PCR (qPCR), the level of expression of the marker genes then being normalized with respect to the level of expression of the two ubiquitous genes according to $\Delta Ct_{gene} = Ct_{gene} - [$(mean value of the) Ct (ubiquitous genes)$]$ to obtain a normalized level of expression $\Delta Ct_{gene}$ for each marker gene the level of expression of which has been measured;

b) comparing the level of expression measured for the marker genes in step a) in said patient against a reference threshold, and for each gene the expression of which has been measured:

i) determining a value $INDEX_{gene}$, which is dependent on the normalized level of expression of the gene, defined by:
$INDEX_{gene} = +1 * \beta$ coefficient of the gene, if $\Delta Ct_{gene} >$ reference threshold of the gene, and
$INDEX_{gene} = -1 * \beta$ coefficient of the gene, if $\Delta Ct_{gene} <$ reference threshold of the gene, and in which the $\beta$ coefficient and the reference threshold ($S_{ref}$) of a given gene are as defined below

| Gene | $S_{ref}$ | $\beta$ coefficient |
|---|---|---|
| NME4 | 3.1864 | −1.3207 |
| ITPR3 | 6.4014 | 1.0850 |
| SESN3 | 3.6262 | 1.0301 |
| ARL4C | 2.6286 | 1.3577 |
| RPLP1 | 6.3748 | 1.0101 | ii) determining for a given patient a value $INDEX_{patient}$ equal to the sum of the $INDEX_{gene}$ of the genes of the combination, and iii) comparing $INDEX_{patient}$ against a final reference threshold previously determined for the combination of genes; and c) administering gemcitabine to the patient if the $INDEX_{patient}$ for the combination of genes is determined to be less than the value of the final reference threshold for the combination of genes, or administering FOLFIRINOX or erlotinib to the patient if the $INDEX_{patient}$ for the combination of genes is determined to be greater than the value of the final reference threshold for the combination of genes.

2. A method for treating pancreatic cancer, comprising administering gemcitabine to a patient suffering from pancreatic cancer at time intervals, and during the interval between treatment with gemcitabine, monitoring the efficacy of treatment by:

a) measuring the level of expression of each gene ($Ct_{gene}$) of a combination of at least NME4 and ARL4C marker genes and optionally ITPR3, SESN3 and/or RPLP1 marker gene(s), and the level of expression of two ubiquitous B2M and GAPDH genes in a blood sample taken from said patient, said levels of expression being measured from the transcription level of the RNA or cDNA of said gene as number of cycle(s) (Ct, "cycle threshold") by real-time quantitative PCR (qPCR), the level of expression of the marker genes then being normalized with respect to the level of expression of the two ubiquitous genes according to $\Delta Ct_{gene} = Ct_{gene} - [(\text{mean value of the}) \, Ct \, (\text{ubiquitous genes})]$ to obtain a normalized level of expression $\Delta Ct_{gene}$ for each marker gene the level of expression of which has been measured;

b) comparing the level of expression measured for the marker genes in step a) in said patient against a reference threshold, and for each gene the expression of which has been measured:

i) determining a value $INDEX_{gene}$, which is dependent on the normalized level of expression of the gene, defined by:
   $INDEX_{gene} = +1*\beta$ coefficient of the gene, if $\Delta Ct_{gene} > $ reference threshold of the gene, and
   $INDEX_{gene} = -1*\beta$ coefficient of the gene, if $\Delta Ct_{gene} < $ reference threshold of the gene,
   in which the $\beta$ coefficient and the reference threshold ($S_{ref}$) of a given gene are as defined below

| Gene | $S_{ref}$ | $\beta$ coefficient |
| --- | --- | --- |
| NME4 | 3.1864 | −1.3207 |
| ITPR3 | 6.4014 | 1.0850 |
| SESN3 | 3.6262 | 1.0301 |
| ARL4C | 2.6286 | 1.3577 |
| RPLP1 | 6.3748 | 1.0101 | ii) determining for a given patient a value $INDEX_{patient}$ equal to the sum of the $INDEX_{gene}$ of the genes of the combination, and iii) comparing the $INDEX_{patient}$ against a final reference threshold previously determined for the combination of genes; and c) proceeding with administering gemcitabine to the patient to continue treatment with gemcitabine at time intervals if the $INDEX_{patient}$ for the combination of genes is determined to be less than the value of the final reference threshold for the combination of genes, or
changing to a non-gemcitabine-based treatment by administering FOLFIRINOX or erlotinib to the patient if the $INDEX_{patient}$ for the combination of genes is determined to be greater than the value of the final reference threshold for the combination of genes.

3. The method according to claim 1, wherein, in step a), the level of expression of three marker genes is measured.

4. The method according to claim 1, wherein said blood sample is a sample of peripheral whole blood.

5. The method according to claim 1, wherein the level of expression of the five marker genes is measured, the final reference threshold being 1.102, an $INDEX_{patient}$ less than 1.102 indicating a prognosis of long-term survival.

6. The method according to claim 2, wherein in step a) the level of expression of three marker genes is measured.

7. The method according to claim 2, wherein said blood sample is a sample of peripheral whole blood.

8. The method according to claim 2, wherein the level of expression of the five marker genes is measured, the final reference threshold being 1.102, an $INDEX_{patient}$ less than 1.102 indicating a prognosis of long-term survival.

9. The method according to claim 1, wherein, in step a), the level of expression of four marker genes is measured.

10. The method according to claim 1, wherein, in step a), the level of expression of five marker genes is measured.

11. The method according to claim 2, wherein, in step a), the level of expression of four marker genes is measured.

12. The method according to claim 2, wherein, in step a), the level of expression of five marker genes is measured.

* * * * *

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: sens PCR primer for NME4
<220> FEATURE:
<221> NAME/KEY: misc_feature
<223> OTHER INFORMATION: synthetic

```
<400> SEQUENCE: 1
catgattgga cacaccgact c                                              21

<210> SEQ ID NO 2
<211> LENGTH: 21
<212> TYPE: DNA
<213> ORGANISM: Artificial Sequence
<220> FEATURE:
<223> OTHER INFORMATION: antisens PCR Primer for NME4
<220> FEATURE:
<221> NAME/KEY: misc_feature
<223> OTHER INFORMATION: synthetic

<400> SEQUENCE: 2
gacgctgaag tcacccctta t                                              21

<210> SEQ ID NO 3
<211> LENGTH: 20
<212> TYPE: DNA
<213> ORGANISM: Artificial Sequence
<220> FEATURE:
<223> OTHER INFORMATION: Sens PCR primer for ITPR3
<220> FEATURE:
<221> NAME/KEY: misc_feature
<223> OTHER INFORMATION: synthetic

<400> SEQUENCE: 3
tcctggggaa gagttgtacg                                                20

<210> SEQ ID NO 4
<211> LENGTH: 20
<212> TYPE: DNA
<213> ORGANISM: Artificial Sequence
<220> FEATURE:
<223> OTHER INFORMATION: antisens PCR primer for ITPR3
<220> FEATURE:
<221> NAME/KEY: misc_feature
<223> OTHER INFORMATION: synthetic

<400> SEQUENCE: 4
aggagaaaaa caagcggtca                                                20

<210> SEQ ID NO 5
<211> LENGTH: 20
<212> TYPE: DNA
<213> ORGANISM: Artificial Sequence
<220> FEATURE:
<223> OTHER INFORMATION: sens PCR primer for SESN3
<220> FEATURE:
<221> NAME/KEY: misc_feature
<223> OTHER INFORMATION: synthetic

<400> SEQUENCE: 5
ttgcctttgt agtcctgtgc                                                20

<210> SEQ ID NO 6
<211> LENGTH: 22
<212> TYPE: DNA
<213> ORGANISM: Artificial Sequence
<220> FEATURE:
<223> OTHER INFORMATION: Antisens PCR primer for SESN3
<220> FEATURE:
<221> NAME/KEY: misc_feature
<223> OTHER INFORMATION: synthetic

<400> SEQUENCE: 6
cattagtcca gtcacgtgct tc                                             22
```

-continued

```
<210> SEQ ID NO 7
<211> LENGTH: 20
<212> TYPE: DNA
<213> ORGANISM: Artificial Sequence
<220> FEATURE:
<223> OTHER INFORMATION: Sens PCR Primer for ARL4C
<220> FEATURE:
<221> NAME/KEY: misc_feature
<223> OTHER INFORMATION: synthetic

<400> SEQUENCE: 7
aaagccctgt ggtgtatcaa                                               20

<210> SEQ ID NO 8
<211> LENGTH: 20
<212> TYPE: DNA
<213> ORGANISM: Artificial Sequence
<220> FEATURE:
<223> OTHER INFORMATION: Antisens PCR primer for ARL4C
<220> FEATURE:
<221> NAME/KEY: misc_feature
<223> OTHER INFORMATION: synthetic

<400> SEQUENCE: 8
gcttcctctg ttgggtcaga                                               20

<210> SEQ ID NO 9
<211> LENGTH: 20
<212> TYPE: DNA
<213> ORGANISM: Artificial Sequence
<220> FEATURE:
<223> OTHER INFORMATION: Sens PCR Primer for RPLP1
<220> FEATURE:
<221> NAME/KEY: misc_feature
<223> OTHER INFORMATION: synthetic

<400> SEQUENCE: 9
tgggctttgg tcttttttgac                                              20

<210> SEQ ID NO 10
<211> LENGTH: 20
<212> TYPE: DNA
<213> ORGANISM: Artificial Sequence
<220> FEATURE:
<223> OTHER INFORMATION: Antisens PCR Primer for RPLP1
<220> FEATURE:
<221> NAME/KEY: misc_feature
<223> OTHER INFORMATION: synthetic

<400> SEQUENCE: 10
cagaccattt ttgcagagca                                               20

<210> SEQ ID NO 11
<211> LENGTH: 23
<212> TYPE: DNA
<213> ORGANISM: Artificial Sequence
<220> FEATURE:
<223> OTHER INFORMATION: Sens PCR Primer for B2M
<220> FEATURE:
<221> NAME/KEY: misc_feature
<223> OTHER INFORMATION: synthetic

<400> SEQUENCE: 11
gctcagtaaa gacacaacca tcc                                           23

<210> SEQ ID NO 12
<211> LENGTH: 21
<212> TYPE: DNA
<213> ORGANISM: Artificial Sequence
```

```
<220> FEATURE:
<223> OTHER INFORMATION: Antisens PCR Primer for B2M
<220> FEATURE:
<221> NAME/KEY: misc_feature
<223> OTHER INFORMATION: synthetic

<400> SEQUENCE: 12
catctgtgga ttcagcaaac c                                              21

<210> SEQ ID NO 13
<211> LENGTH: 19
<212> TYPE: DNA
<213> ORGANISM: Artificial Sequence
<220> FEATURE:
<223> OTHER INFORMATION: Sens PCR Primer for GAPDH
<220> FEATURE:
<221> NAME/KEY: misc_feature
<223> OTHER INFORMATION: synthetic

<400> SEQUENCE: 13
atggggaagg tgaaggtcg                                                 19

<210> SEQ ID NO 14
<211> LENGTH: 22
<212> TYPE: DNA
<213> ORGANISM: Artificial Sequence
<220> FEATURE:
<223> OTHER INFORMATION: Antisens PCR primer for GAPDH
<220> FEATURE:
<221> NAME/KEY: misc_feature
<223> OTHER INFORMATION: synthetic

<400> SEQUENCE: 14
ggggtcattg atggcaacaa ta                                             22
```